United States Patent
Daniel et al.

(10) Patent No.: US 7,305,308 B2
(45) Date of Patent: Dec. 4, 2007

(54) GAS FLOW METHOD FOR DETECTION OF PREFORM DEFECTS BASED ON TRANSIENT PRESSURE MEASUREMENT

(75) Inventors: Isaac M. Daniel, Morton Grove, IL (US); Sun Kyoung Kim, Hanam (KR)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 11/030,719

(22) Filed: Jan. 6, 2005

(65) Prior Publication Data

US 2005/0177320 A1 Aug. 11, 2005

Related U.S. Application Data

(63) Continuation-in-part of application No. 10/611,318, filed on Jul. 1, 2003, now Pat. No. 6,853,925.

(51) Int. Cl.
*G01B 5/28* (2006.01)
*B29C 45/17* (2006.01)

(52) U.S. Cl. .......................... 702/35; 264/40.3

(58) Field of Classification Search ............... 702/35, 702/38; 425/127; 264/40.7, 2.4, 40.3, 40.6; 703/7; 700/204; 73/38
See application file for complete search history.

(56) References Cited

U.S. PATENT DOCUMENTS

| | | | | |
|---|---|---|---|---|
| 3,971,689 A | * | 7/1976 | Peppler | 162/226 |
| 4,347,069 A | * | 8/1982 | Haney et al. | 65/417 |
| 4,387,833 A | * | 6/1983 | Venus, Jr. | 222/95 |
| 4,940,563 A | * | 7/1990 | Kromrey | 264/257 |
| 5,045,251 A | * | 9/1991 | Johnson | 264/408 |
| 6,532,799 B2 | * | 3/2003 | Zhang et al. | 73/38 |
| 6,853,925 B2 | | 2/2005 | Daniel et al. | 702/35 |
| 2002/0046596 A1 | | 4/2002 | Zhang et al. | 73/38 |

OTHER PUBLICATIONS

Dimension prediction and control for resin transfer molding process; Proceedings of SAMPE Conference; pp. 1-14; May 11-15, 2003; C. Dong et al.

Gas assisted real-time assessment of whole-field permeability profile of fiber preform for liquid composite molding processes; Proceedings of SAMPE Conference; pp. 1-13; May 11-15, 2003; C. Zhang et al.

(Continued)

*Primary Examiner*—John Barlow
*Assistant Examiner*—Toan M. Le (57) ABSTRACT

Method and apparatus to detect and characterize a defect in a fiber preform residing in a preform-receiving cavity of a mold or simulated mold of the type used for liquid composite molding (e.g., resin transfer molding) to make a composite component or structure. The defect may result from fiber preform misplacement in the cavity, accidental inclusions, preform density variations, and/or distortion of the preform. Transient gas or other fluid pressures at multiple locations of the cavity are measured during changing of fluid pressure in the cavity. The measured transient pressures, or data derived therefrom, are analyzed to determine membership of the fiber preform in one of two or more groups that include a standard defect-free group and a defective group, whereby the method determines if the fiber preform or its position in the cavity deviates from the standard defect-free group.

25 Claims, 10 Drawing Sheets

OTHER PUBLICATIONS

Optimal control of accelerator concentration for resin transfer molding process; International Journal of Heat and Mass Transfer, vol. 46, pp. 3747-3754, 2003, S.K. Kim et al.

Gas Flow Method for Detecting Local Preform Defects by Inverse Estimation of Space-varying Permeability; Journal of Composite Materials, vol. 37, No. 15, pp. 1367-1383, 2003, S.K. Kim et al.

Deterimination of three-dimensional permeability of fiber preforms by the inverse parameter estimation technique; Composites: Part A, vol. 34, pp. 421-429, 2003, S.K. Kim et al.

Determination of In-Plane Permeability of Fiber Preforms by the Gas Flow Method Using Pressure Measurements; Polymer Composites, vol. 24, No. 1, pp. 34-44, 2003, S.K. Kim et al.

Determination of permeability of fibrous medium considering inertial effects; Int. Comm. Heat Mass Transfer, vol. 29, No. 7, pp. 879-885, 2002, S.K. Kim et al.

Detection of local preform defects by gas flow method and statistical analysis; Advanced Composites Letters; vol. 12, No. 3, pp. 109-114, 2003, S.K. Kim et al.

In-Situ quality control of RTM preforms by the gas flow method; 48th International SAMPE Symposium, pp. 1702-1713, May 11-15, 2003.

Solution to inverse heat conduction problem in nanoscale using sequential method; Numerical Heat Transfer, Part B; vol. 44; pp. 439-456, 2003, S.K. Kim et al.

In-situ measurement and monitoring of fiber preform permeability for liquid composite molding; Proceedings of the 45th International SAMPE Symposium, vol. 45, p. 2053, 2000, Z. Liang et al.

Gas flow method for detection of local preform defects based on statistical analysis; Proceedings of ICCM 14 Conference; pp. 1-8 Jul. 14-18, 2003; S.K. Kim and I.M. Daniel.

New set-up for measurement of permeability properties of fibrous reinforcements for RTM; Composites: Part A, vol. 33, pp. 959-969, 2002, K. Hoes et al.

Permeability Measurement and Flow Simulation Through Fiber Reinforcement; Polymer Composites; vol. 17, No. 1, pp. 34-42, Feb. 1996, R. Gauvin et al.

A control volume finite-element method for two-dimensional fluid flow and heat-transfer; Numerical Heat Transfer, vol. 6, pp. 245-261, 1983, B.R. Baliga et al.

A gas flow method for determination of in-plane permeability of fiber preforms; Polymer Composites, vol. 22, No. 1, pp. 47-56, 2001, M.K. Um et al.

Statistical characterization of fiber permeability for composite manufacturing; Polymer Composites, vol. 21, No. 6, pp. 996-1006, Dec. 2000, R. Pan et al.

Gas flow test of Braided Preform Quality for Resin Transfer Molding; Advanced Composites Letters, vol. 12, No. 4, pp. 161-163, Sep. 2003, S.K. Kim et al.

Sawley et al., Modelling of Flow in Porous and Resin Transfer Moulding Using Smoothed Particle Hydrodynamics, Dec. 6-8, 1999, Second International Conference on CFD in the Minerals and Process Industries, Australia.

Berker et al., Sensor Based Modeling and Control of Fluid Flow in Resin Transfer Molding, Oct. 1998, Journal of Materials Processing & Manufacturing Science, vol. 7, pp. 195-214.

Mathur et al., Optimization of Gate and Vent Locations for Resin Infusion Processes Using Genetic Algorithms, Jun. 1998, Proceeding of the American Control Conference, Philadelphia, pp. 2176-2180.

Sevostianov et al., Mathematical Model of Cavitation During Resin Film Infusion Process, 2000, Composite Structures, vol. 48, pp. 197-203.

In-situ measurement and monitoring of fiber preform permeability for liquid composite molding, 45th International SAMPE Symposium, pp. 1-10, 2000, Z. Liang et al.

A permeability database for composites manufacturing, Polymer Composites, 18 (5) , pp. 623-633, Oct. 1997, R. Parnas et al.

New sensor-based set-up for permeability-identification, Proc. Of Third Canadian Conf. on Composites (CANCOM 2001), Session 2A1, pp. 1-8, 2001, K. Hoes et al.

* cited by examiner

GAS FLOW METHOD FOR DETECTION OF PREFORM DEFECTS BASED ON TRANSIENT PRESSURE MEASUREMENT

This application is a continuation-in-part application of application Ser. No. 10/611,318 filed Jul. 1, 2003, now U.S. Pat. No. 6,853,925 and claims benefits and priority thereof.

CONTRACTUAL ORIGIN OF THE INVENTION

The United States Government may have rights in this invention pursuant to Contract No. N00014-02-C-0087 between the Office of Naval Research and Northwestern University, Evanston, Ill.

FIELD OF THE INVENTION

The present invention relates to detection and characterization of defects associated with a fiber preform in a mold cavity of the type used for liquid molding of composite components or structures.

BACKGROUND OF THE INVENTION

The resin transfer molding (RTM) process has become a popular composite manufacturing process due to its suitability for high volume production and cost effectiveness. In this process, the dry fiber reinforcement (preform) is enclosed in the mold and resin is injected and allowed to cure [see reference 1].

The impregnation of the fluid resin into the preform is defined by the permeability of the reinforcement, which is the ability of a Newtonian fluid to permeate a porous medium with a sufficiently low Reynolds number, as given by Darcy's Law. The permeability of an undistorted preform with a constant fiber volume ratio can be assumed to be uniform over the entire domain; however, the permeability can be significantly altered by defects, distortions, or other anomalies in the preform. Such drastic changes in local permeability can affect resin flow patterns, rendering portions of the mold to be insufficiently filled. Permeability variations within a preform can be attributed to a number of factors, such as improper preform preparation, misplacement or shifting in the mold, accidental inclusion of foreign material, natural surface density variation of the preform, etc. If such occurrences were not detected prior to resin injection, the potential for costly part scrapping would be increased [see references 2 and 3]. Aside from the additional voids due to permeability non-uniformities, preform distortions could contribute to residual stresses and stress concentrations during in-service loading. Early detection, therefore, of such reinforcement irregularities is critical for effective quality control.

Conventional methods for permeability measurement rely on oils or other viscous fluids to be injected into the reinforcement. These fluids soil the fibers and cannot be removed without damage to the preform. Furthermore, the bulk material permeability data obtained from such tests would not provide the information regarding local permeability variation, which is necessary for locating defects. Such strategies, therefore, could not logically be applied in-situ prior to an RTM run. Methods, however, providing multiple pressure measurements with a gas, like the gas flow method, are well suited for such applications.

Published U.S. Patent Application US 2002/0046596 A1 describes a system for in-situ and on-line monitoring of a preform quality for liquid composite molding using flow of a gas through the preform in the mold cavity. Pressure transducers communicated to openings in a lower mold section provided sensed gas pressure values to a data acquisition and processing device having software which generates a pressure profile of the gas flow for the preform. This pressure profile is evaluated by comparing it with a theoretically calculated pressure profile. The method described in the patent application is inherently one-dimensional and was not proven with preform materials having varying degrees of anisotropy. Furthermore, it requires prior determination of the permeability of the preform material.

Liang et al. suggested the possibility of using the gas flow method for defect detection by measuring permeability of a preform with a rectangular cutout region [reference 4].

Copending U.S. application Ser. No. 10/611,318 filed Jul. 1, 2003, by Daniel, Kim, and Opperer describes a gas flow method for detecting and characterizing defects associated with a fiber prefrom using steady state or constant flow of gas through the preform in the mold cavity [also see references 2-3]. In this steady state gas flow method, pressure data are obtained at a plurality of ports communicated to the mold cavity during steady state gas flow. The pressure data is statistically analyzed by discriminant analysis and compared with reference data from a similar gas flow test using a good (high quality) preform. Each steady state test generates a single data point for a partcicular preform for the comparison. The magntiude of deviation of a preform from the reference data is used to determine whether the preform is defective or not.

SUMMARY OF THE INVENTION

The present invention relates to detection of a defect asscoiated with a fiber preform residing in a preform-receiving cavity of a mold or simulated mold of the type used for liquid composite molding (e.g. resin transfer molding) to make a composite component or structure. The defect may result from fiber preform misplacement in the cavity, accidental inclusions, preform density variations, and/or distortion of the preform. In an illustrative embodiment of the invention, method and apparatus pursuant to an embodiment of the invention involve providing a changing fluid pressure (e.g. decreasing or increasing gas pressure) in the cavity containing the fiber preform and measuring time-varying (transient) fluid pressure over time at one or more locations of the cavity during changing of the pressure therein. The measured transient fluid pressures, or data derived therefrom, can be analyzed to determine membership of the fiber preform in one of two or more groups that include a standard defect-free group and a defective group. The method thereby determines if the fiber preform or its position in the cavity deviates from the standard defect-free group. In one embodiment of the invention, the data derived from the measured transient gas pressures comprises local permeability variations of the preform calculated using the measured transient gas pressure data.

Pursuant to a particular embodiment of the invention, a preform-receiving cavity having a fiber preform therein is gas pressurized to a given superambient pressure. Then, a vent of the cavity is opened to vent the cavity to ambient atmosphere, thereby depressurizing the cavity so as to decrease gas pressure therein. Transient gas pressures are measured over time at each of multiple locations as the gas pressure in the cavity decreases. The measured transient pressures, or data derived therefrom, are analyzed to determine membership of the fiber preform in one of two or more groups that include a standard defect-free group and a defective group. The analysis can involve comparing the transient pressures of the particular tested preform to a data base of transient pressures generated from previously tested preforms. Alternately or in addition, the measured transient gas pressures for the particular tested preform can be analyzed by statistical analysis.

The invention is advantageous in that large amounts of time-varying fluid pressure data can be generated from a single test of a fiber preform in a cavity and used to detect a defect associated with the fiber preform or its position in the cavity. Other advantages and details of the present invention will be more readily apparent from the following detailed description taken in conjunction with the following drawings.

DESCRIPTION OF THE INVENTION

The present invention relates to detection of a defect asscoiated with a fiber preform enclosed in a cavity of a mold or simulated mold of the type used for liquid composite molding (e.g. resin transfer molding) to make a composite component or structure wherein the method involves providing a changing fluid pressure (e.g. decreasing or increasing gas pressure) in the cavity containing the fiber preform, measuring time-varying (transient) fluid pressure with time at each of one or more locations of the cavity during changing of the fluid pressure in the cavity, and analyzing the measured transient fluid pressures, or data derived therefrom, to determine membership of the fiber preform in one of two or more groups that include a standard defect-free group and a defective group. The defect may result from fiber preform misplacement in the cavity, accidental inclusions, preform density variations, and/or distortion of the preform. The method and apparatus of the invention can determine if the fiber preform or its position in the cavity deviates from the standard defect-free group.

Figure 1:
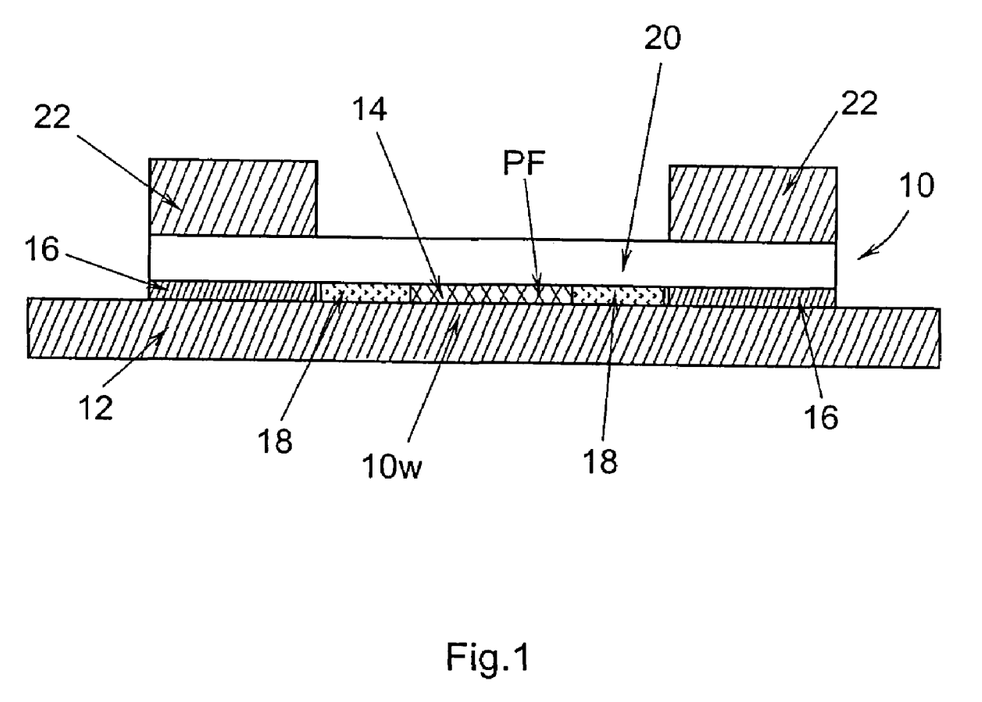
FIG. 1 is a schematic transverse sectional view of a simulated molding apparatus shown without the clamps and used in practicing an illustrative embodiment of the invention.
Figure 2:
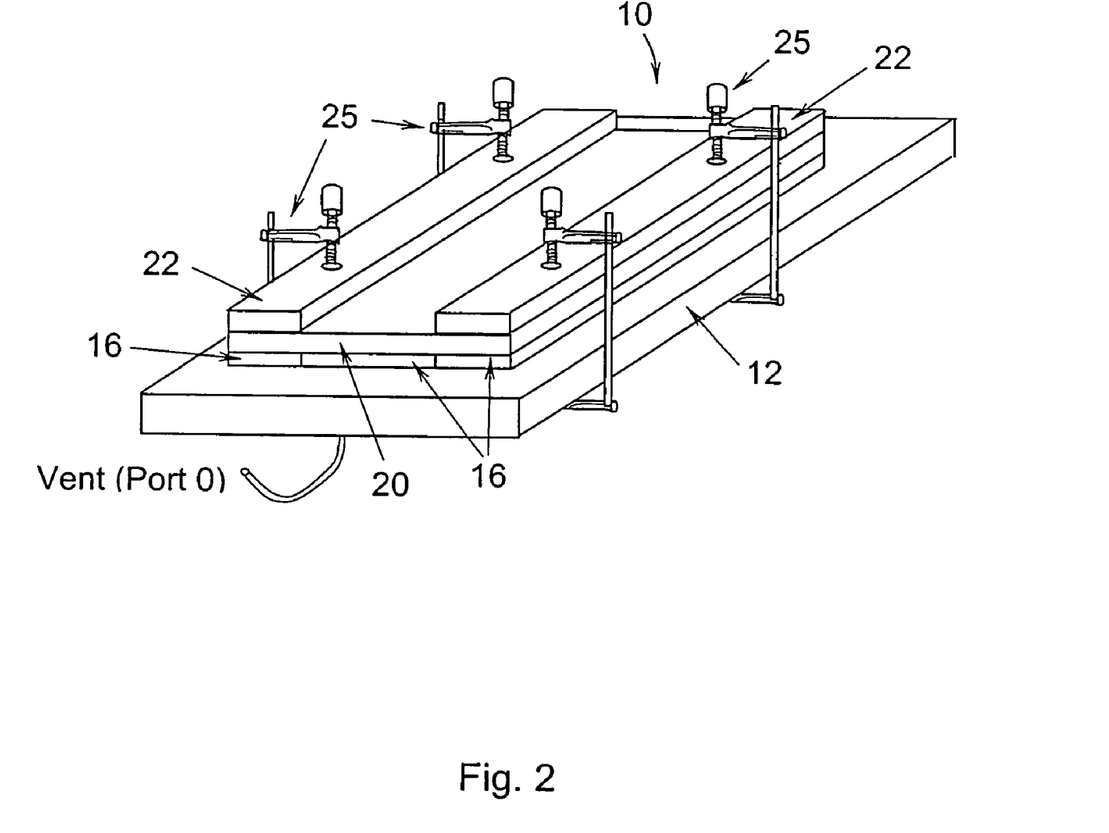
FIG. 2 is a perspective view of the molding apparatus with the clamps shown.

For purposes of illustration and not limitation, the invention will be described with respect to experiments conducted in a simulated one-dimensional resin transfer mold 10 shown in FIGS. 1 and 2 having a simulated preform-receiving mold cavity 14 for receiving a preform PF. The mold includes ports numbered 0, 1, 2, 3, 4, and 5 shown in FIGS. 3-4 spaced apart in a row on a mold wall 10w along the length of the molding cavity 14 and communicated to the cavity 14 for obtaining gas pressure measurements using pressure transducers PT. In practicing the experimental procedure, the cavity 14 containing the preform PF is pressurized to a certain gas pressure, and then the vent (port 0) is suddenly opened to atmosphere, decreasing gas pressure in the cavity 14. During this process, the gas pressure variation with time at each of various locations at the ports on the mold wall 10w is recorded. The acceptability of a test preform is determined by comparing test data from a prefrom associated with an anomaly to a reference data base of transient pressures generated from previously tested preforms. Although the experiments are described below in detail for a one-dimensional variation of gas pressures along the cavity 14 and thus the preform for simplicity of method verification, the method of the invention is not so limited and can be practiced with respect to multi-dimensional variations of transient gas pressures using preforms of complex geometry. Moreover, although the experiments are described below with respect to a changing gas pressure in the simulated preform-receiving molding cavity, the invention envisions using any fluid such as a liquid to provide a changing fluid pressure therein.

Analytical

Consider the pressure p(x,t) for one-dimensional gas flow, where x is the distance from the vent (port 0) of the mold cavity and t is time. In the Darcy flow regime, the velocity in the x-direction, u, is expressed as u=−K∂p/∂x. The mass conservation of gas in the one-dimensional Darcy flow is described as ∂p/∂t+∂(ρu)/∂x=0 where ρ is the density of the gas. Assuming that the gas is an ideal gas, the density is determined by ρ=p/RT. Combining the above three equations for velocity, mass conservation and ideal gas law, we have $$\frac{\partial p}{\partial t} - \frac{K}{\mu}\frac{\partial}{\partial x}\left(p\frac{\partial p}{\partial x}\right) = 0 \qquad (1)$$

The governing equation is linearized for convenience. In the actual gas flow test, the pressure variation should be very small in comparison with the atmospheric pressure to maintain the validity of Darcy's law. Considering that $p\partial^2 p/\partial x^2 \ll (\partial p/\partial x)^2$ and $p/p_o \approx 1$, where $p_o$ is the initial pressure, the above expression can be linearized as follows.

$$\frac{\partial p}{\partial t} - \frac{p_0 K}{\mu}\frac{\partial^2 p}{\partial x^2} = 0 \qquad (2)$$

There is an exact analytical solution for this pressure field problem. Let us introduce the following dimensionless variables.

$$p^+ = \frac{p}{p_o}, x^+ = \frac{x}{L}, t^+ = \frac{p_o K}{\mu L^2} t \quad (3)$$

where L, μ and K are the domain length, viscosity and permeability, respectively. Length is that of the mold cavity or preform, viscosity is that of the gas or any fluid used, and permeability is that of the preform. The governing equation is non-dimensionalized as $$\frac{\partial p^+}{\partial t^+} = \frac{\partial^2 p^+}{\partial x^{+2}}, 0 < x^+ < 1 \quad (4)$$

The initial and boundary conditions are $$p^+(x^+,0)=1 \text{ for } 0 \leq x^+ \leq 1 \quad (5)$$

$$p^+(0, t^+) = 0 \text{ and } \left.\frac{\partial p^+}{\partial x^+}\right|_{x^+=1} = 0 \text{ for } t^+ > 0 \quad (6)$$

Figure 5:
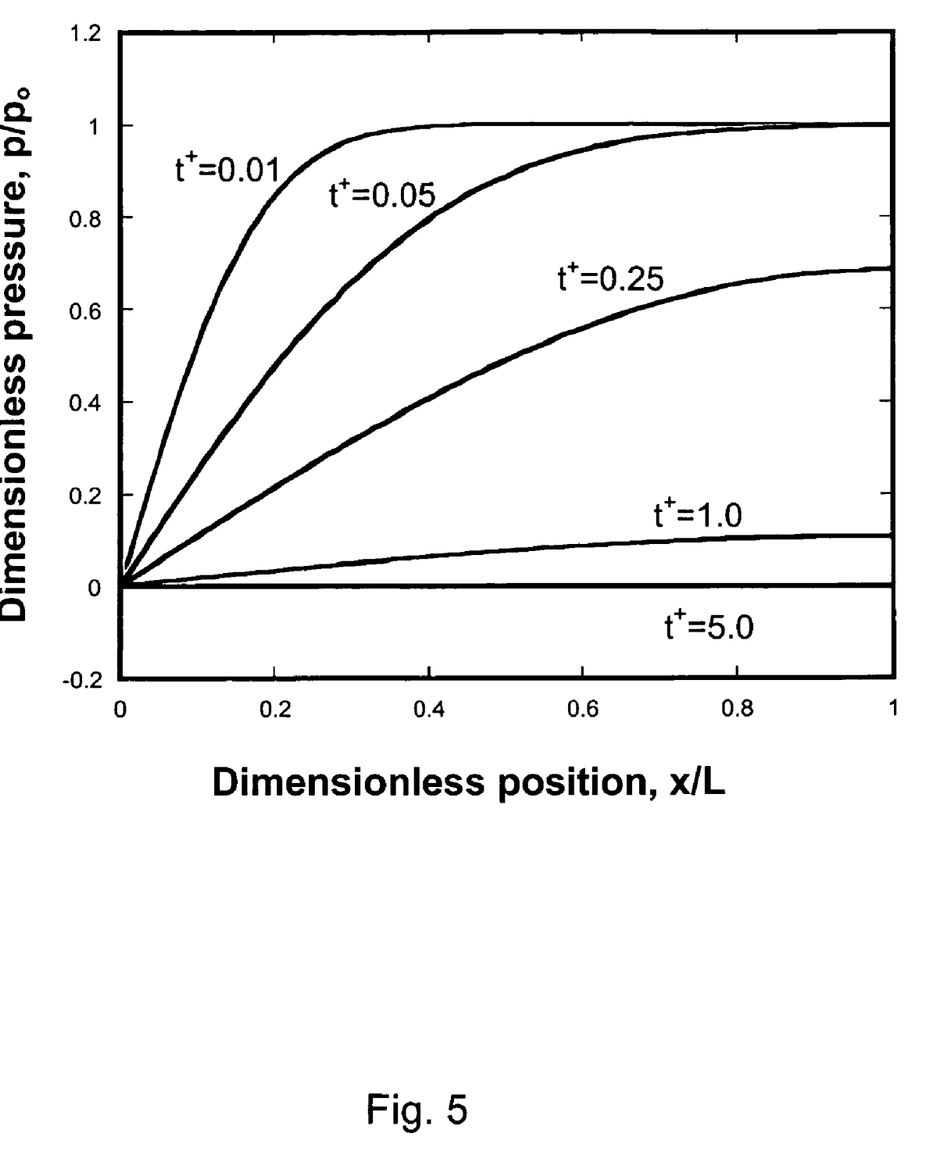
FIG. 5 is a graph showing calculated dimensionless gas pressure versus dimensionless time curves at different times $t^+$ illustrating the physical phenomenon of changing pressure profiles with time at the ports. All quantities in FIG. 5 are dimensionless so that the results are applicable for molds of any length, pressurized to any initial pressure, with a liquid of any viscosity and a preform of any permeability.

For the above problem, the exact solution is given as [6]

$$p^+(x^+, t^+) = 2\sum_{n=1}^{\infty} \frac{1}{\lambda_n} \exp(-\lambda_n^2 t^+) \sin \lambda_n x^+ \quad (7)$$

where $\lambda_n = (2n-1)\pi/2$. FIG. 5 shows results of a sample calculation with the pressure curves illustrating the physical phenomenon of changing gas pressure profiles with time. All quantities in FIG. 1 are dimensionless so that the results are applicable for molds of any length, pressurized to any initial pressure, with a liquid of any viscosity and a preform of any permeability.

If the permeability of the enclosed preform PF is to be determined in order to conduct further analyses, the permeability can be obtained from the transient gas pressure measurements by the inverse parameter estimation technique [see reference 7-9]. The permeability, K, is the value that minimizes the following least-squares expression.

$$S(K) = \sum_{k=1}^{N} \int_{t=0}^{t=t_f} [p_k(t; K) - \bar{p}_k(t)]^2 dt \quad (8)$$

This formulation considers measurement of pressure at N different locations in the flow domain. The least squares norm, S(K), stands for deviation of measured pressure variation from the calculated one. The inverse parameter estimation technique allows finding K that minimizes S(K). Minimization of S(K) means minimal deviation between measured and calculated pressures over the selected time interval. The solution procedure of this inverse problem is very similar to that of the inverse heat conduction problem of thermal diffusivity estimation [reference 6]. To solve the optimization problem numerically, the Levenberg-Marquardt method is employed [reference 10]. An existing optimization code (BCLSJ) was employed for the implementation of the inverse method [see reference 11].

The permeability determination is accomplished with a set of reference data (transient gas pressure data measured at ports 1, 2, 3, 4, and 5) obtained from a well controlled experiment. The experimental data is normalized in dimensionless form using the estimated permeability by Eq. (3).

Experimental Procedure

Figure 4:
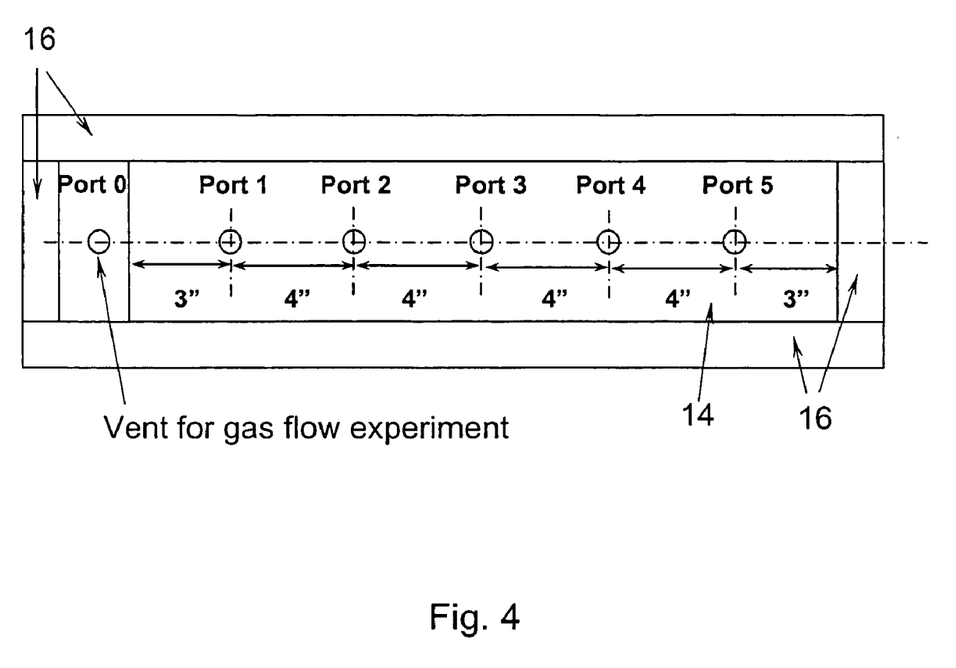
FIG. 4 is view showing locations of ports on the steel mold wall along the length of the cavity for obtaining gas pressure measurements.

The mold 10 used in experimental tests can be constructed without any machining by simply assembling commercially available plates and bars. For example, a lower steel plate 12 (1 inch thick) on which the fiber preform PF is placed has six ports numbered 0, 1, 2, 3, 4, and 5 spaced apart in a row on the lower steel mold wall 10w along the length of the simulated preform-receiving mold cavity 14 as shown in FIG. 4. To maintain the thickness of the cavity 14 constant, a pair of steel shims 16 of 3.17 mm (⅛ inch) thickness were placed over the steel plate 12. End shims 16 also were placed on the plate 12. The steel shims 16 formed a rectangular cavity 14 on the steel plate 12, FIG. 4. Sealant tape 18 (available as Tacky Tape, SM5126 vacuum bag sealant tape) was applied to the plate 12 between the preform PF and the shims 16, FIG. 1. A 25 mm (1 inch) thick transparent acrylic closure plate 20 was placed over the steel shims 16 and preform PF to form the upper wall of the cavity 14. A pair of shims 22 of 38 mm (1.5 inch) thickness were laid on the transparent closure plate 20 to stiffen the transparent plate 20 and apply clamping force via clamps 25 toward the steel plate 12. However, the invention envisions practicing the method in a preform-receiving cavity of an actual RTM mold and/or of an identical simulation of the actual RTM mold to detect a defect associated with a fiber preform residing in the cavity of the mold. If the preform is tested in the actual mold, the pressure transducer ports may be closed off with plugs placed therein in lieu of the tubing T or otherwise closed off prior to conducting the RTM process. In another embodiment of the invention, initial testing of a fiber preform in the identical simulation of the actual mold can be used to determine whether the defect is acceptable or not before the fiber preform is subsequently placed in the actual mold for conducting the actual RTM process.

Figure 3:
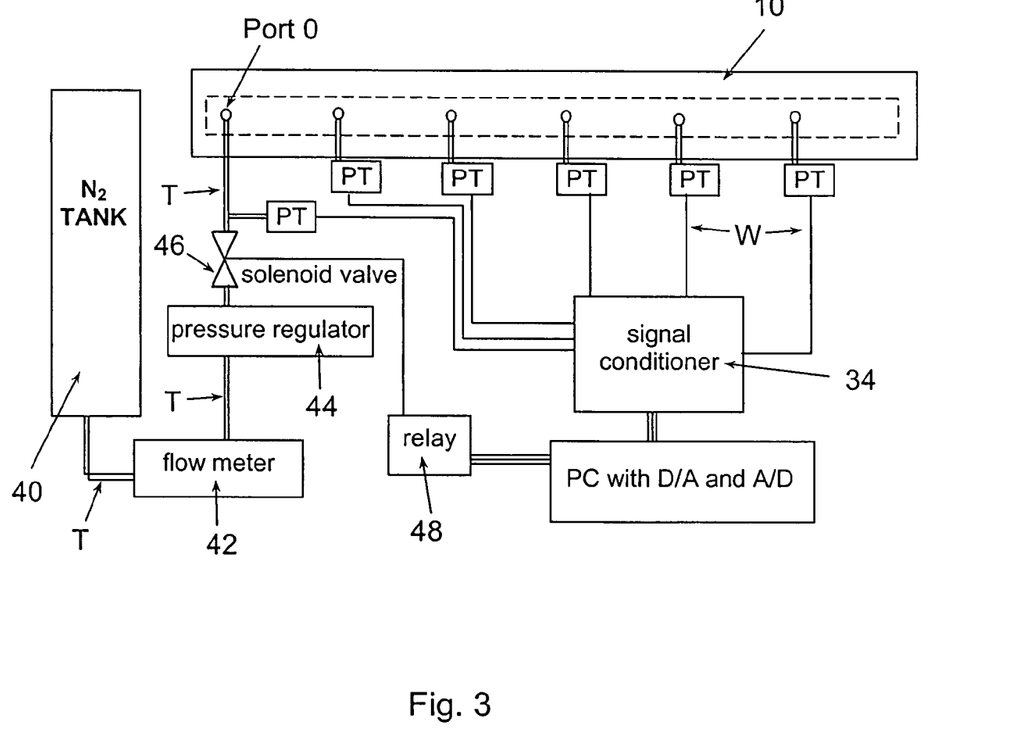
FIG. 3 is a schematic view of the molding apparatus and defect detection apparatus having gas pressure source and data measuring and accumulation devices used in the illustrative embodiment of the invention.

A schematic view of the experimental setup using the mold 10 is shown in FIG. 3. Pressure transducers PT (Omega, PX2650) were connected to the ports 0, 1, 2, 3, 4, and 5 in the lower steel plate 12 so as to communicate to the cavity 14 via mold wall 10w to record the pressure variation over time during the release of gas from the cavity 14. Pressure readings from the transducers PT were sent via wiring W and recorded into storage of conventional computer storage PC via a signal conditioning system 34 that comprised a filter and an amplifier to condition the signals from the pressure transducers for input into the AD (analog to digital) converter in the computer.

The fiber preform PF used in the experimental tests comprised twelve layers of a unidirectional glass fiber preform (Hexcel, SA047, plain heatset available from Hexcel Corp.) laid one on top of each other in the cavity 14. The invention is not limited for use with any particular fiber preform, however, since other types of fiber preforms can be tested pursuant to the invention.

The experimental procedure was as follows. After pressurizing the cavity 14 having the preform PF enclosed therein with nitrogen gas from nitrogen gas source 40 via a flow meter 42 (Omega, FMA-A2305) and pressure regulator 44 (Omega, FMA-A2407) and tubing T shown in FIG. 3, the solenoid valve 46 at the vent (port 0) was fully opened at t=0 s suddenly where t is the time. This means the pressure at the vent (port 0) was maintained at atmospheric pressure ($p^+=0$) for $t^+>0$. Following this sudden release of pressure, pressure variations were measured over time at multiple ports 1, 2, 3, 4, and 5 located along the length of the cavity 14 as shown in FIG. 4. Deviations in the gas flow phenomenon can be detected by comparing the time-varying gas pressures of reference and test fiber preforms PF described below for example. Opening/closing of the solenoid valve 46 was controlled by computer PC using relay 48.

Four different experimental setups were used. The pertinent experimental parameters are listed in Table 1 where "nominal gap" is the distance or gap between the metal shims 16 and the preform edges. In the first setup, Setup 1, tacky sealant tape (sealant) was inserted between the metal shims 16 and the lateral edges of the preform PF, FIG. 1, to prevent racetracking where racetracking involves faster flow along the preform edges. Setup 1 is the reference Setup against which the other Setups 2, 3, and 4 are compared.

In Setup 2, the preform directly contacts the metal shims 16 (i.e. no tacky sealant tape was used) such that Setup 2 simulates the more realistic situation in an RTM mold, where the metal wall of the mold makes direct contact with the lateral edges of the preform.

In Setup 3, a narrow open gap of 0.2 mm width was created between the metal shims 16 and the lateral edges of the preform PF by inserting and removing a 0.1 mm gage between each metal shim 16 and preform before mold assembly. In Table 1, the designation "metal shim" means that the metal shim 16 extended up to or close to the edge of the preform without use of sealant tape.

Setup 4 was similar to Setup 1 with the addition of a piece of thick paper of 0.008 inch thickness (not shown) simulating an inclusion inserted on top of the preform beneath the transparent closure plate 20 at a location between ports 2 and 3.

Throughout the experiments, the cavity 14 was pressurized to $p_o=0.142$ kPa (gage pressure). Thus, the assumption used for linearization of the governing equation, $p/p_o=101.3/(101.3+0.142)\approx 1$, is valid.

TABLE 1

| | Experimental Cases | | | |
|---|---|---|---|---|
| Setup | 1 (Reference) | 2 | 3 | 4 |
| Nominal Gap | 0 mm | 0 mm | 0.2 mm | 0 mm |
| Preform contact | Tacky tape | Metal shim | Metal shim | Tacky tape |
| Inclusion | None | None | None | Thick paper between ports 2 and 3 |

Results and Discussion

Figure 6:
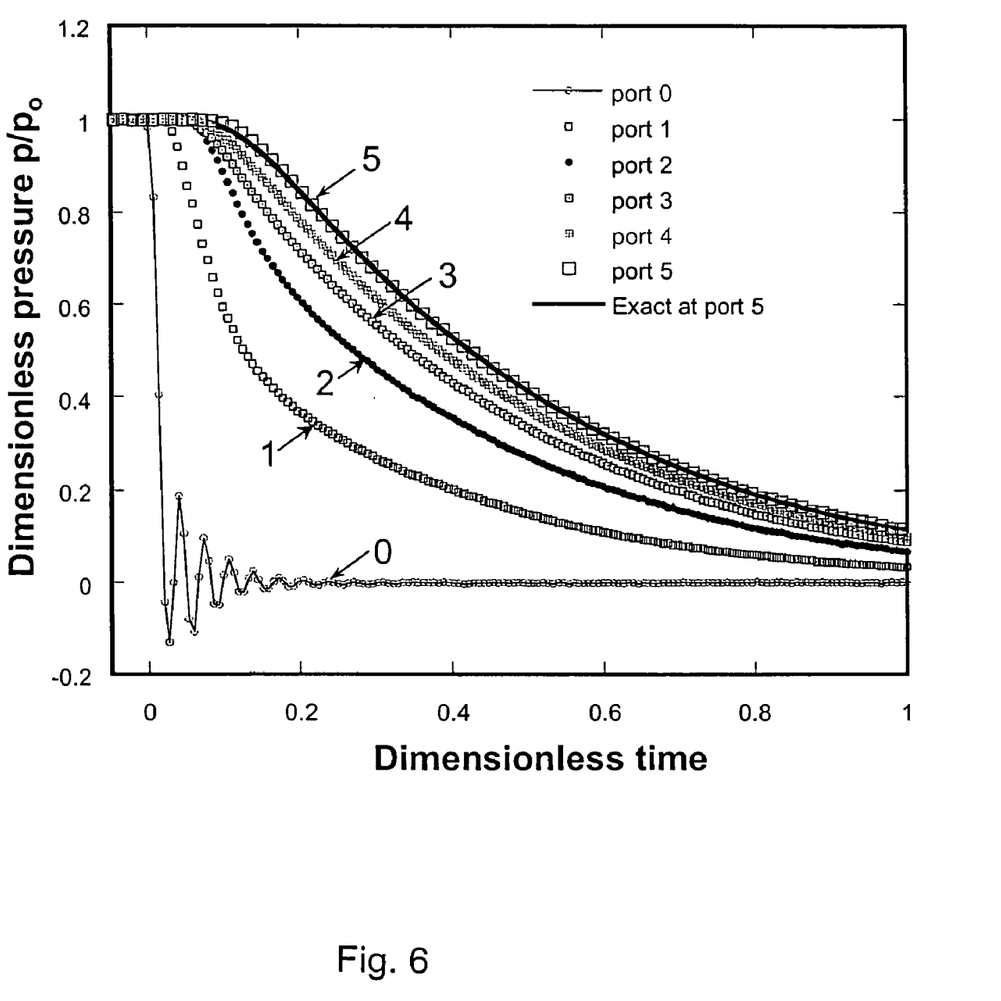
FIG. 6 is a graph of dimensionless gas pressure versus dimensionless time for Setup 1 at ports 0, 1, 2, 3, 4, and 5 where each graph is designated by the port number.

In both Setup 1 and 2, the nominal gap was kept to the minimum possible. Setup 1 is for the reference case. Thus, the data obtained for Setup 1 is regarded as data from a defect-free preform. The data for ports 0, 1, 2, 3, 4, and 5 are shown in FIG. 6. This figure compares experimental and exact analytical data obtained by Eq. (7) at Port 5 ("Exact at port 5"). As can be seen, both sets of data coincide exactly throughout the entire time domain. The experimental data points at Port 0 show the boundary condition of the problem (Eq. (6)). In this sort of physical system, the pressure cannot drop suddenly to the designated state. As shown in the figure, a slight time lag and noticeable fluctuation near the edge are observed. The time lag is due to the sensor, and solenoid valve response time and the fluctuation is mainly due to the surge.

Figure 7:
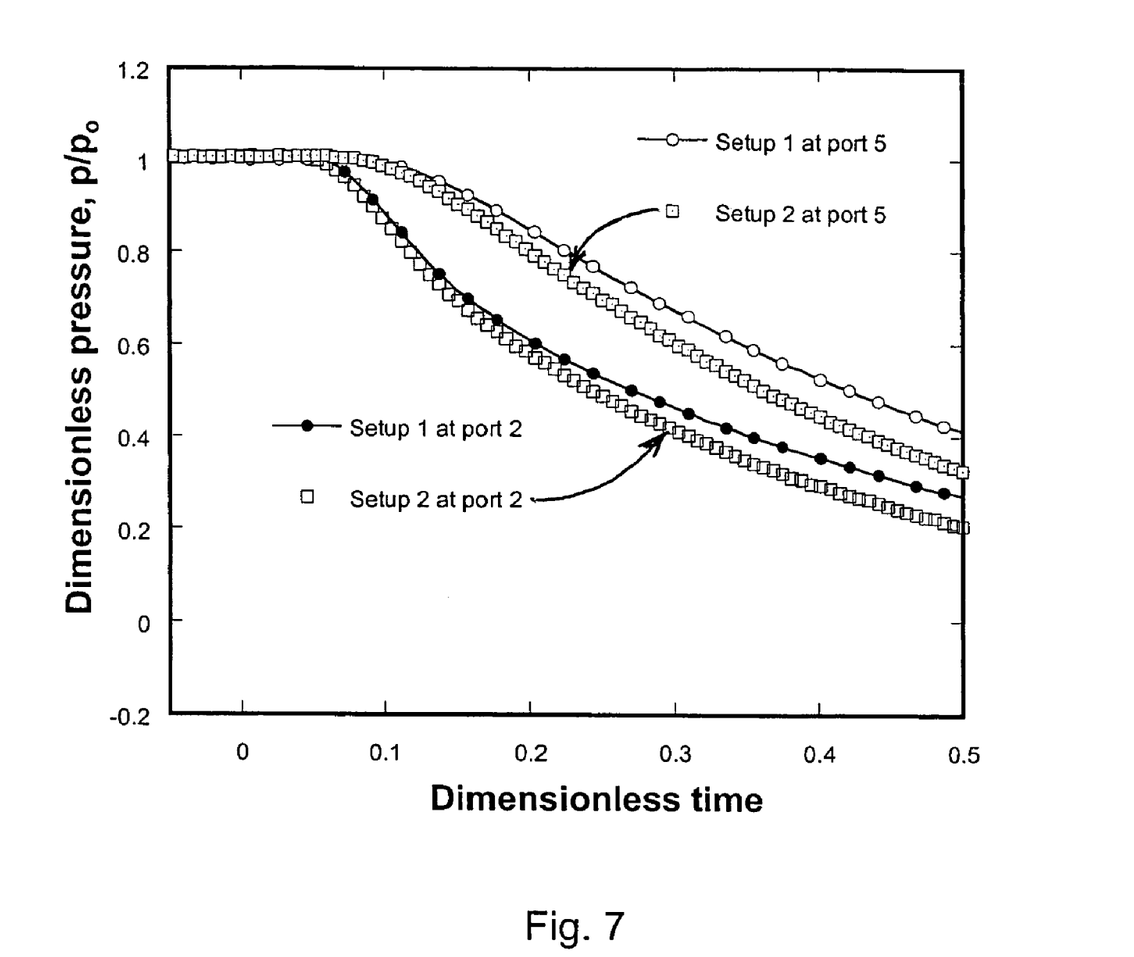
FIG. 7 is a graph of dimensionless gas pressure versus dimensionless time for Setup 1 and 2 at ports 2 and 5.
Figure 8:
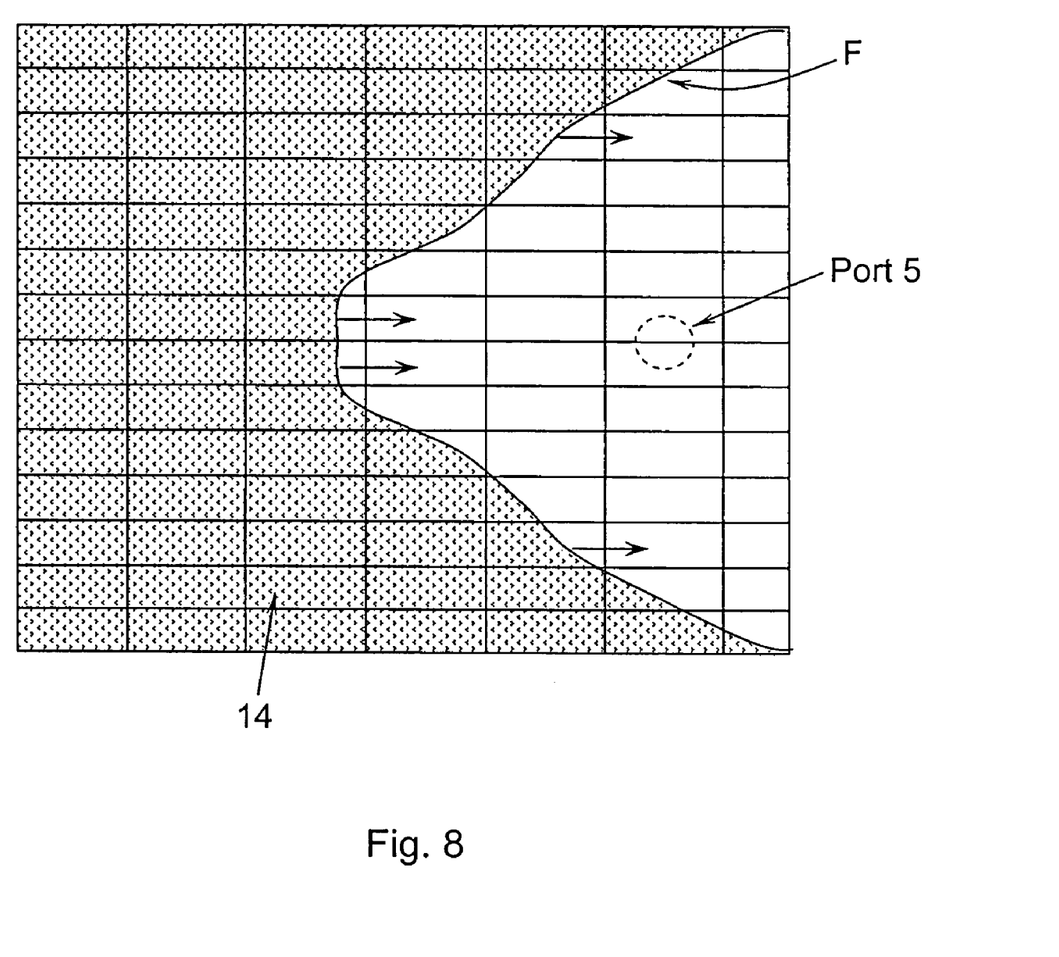
FIG. 8 is a view of the flow pattern of liquid soap injected in the cavity showing race tracking in Setup 2.

A comparison between results of Setup 1 and 2 at ports 2 and 5 is shown in FIG. 7. It is observed that the rate of pressure drop in the reference case, Setup 1, is significantly lower. This means that racetracking can be detected by the gas flow test prior to resin injection. Liquid soap was injected in the mold in Setup 2 to observe the flow. FIG. 8 shows a wedge shaped flow front F due to racetracking in Setup 2 at the edges of the preform in the cavity 14 after liquid soap was injected at port 0, which is left and outside of the figure, and as the flow front moves from left to right at some location in the cavity 14 between port 1 and port 5.

Figure 9:
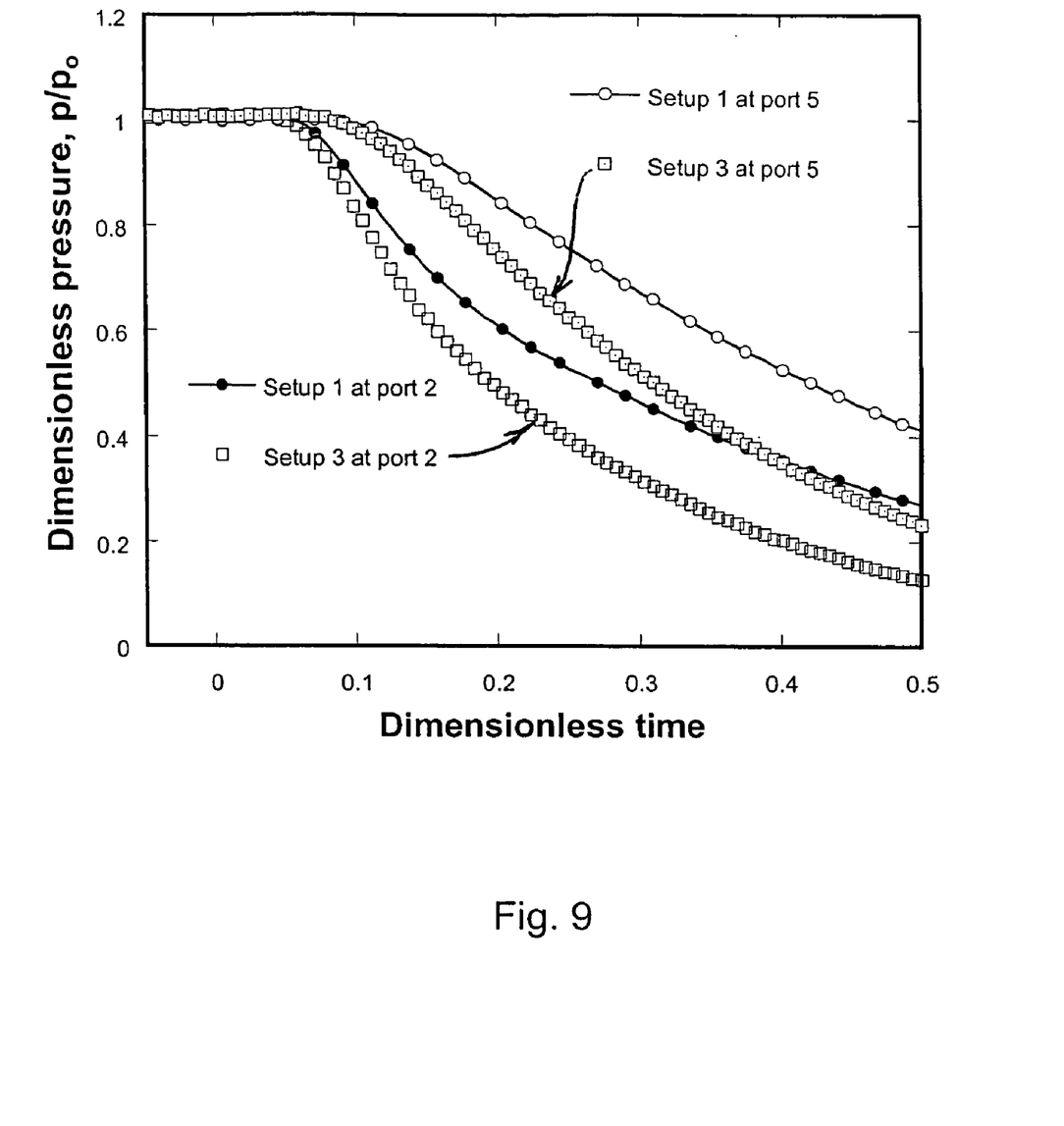
FIG. 9 is a graph of dimensionless gas pressure versus dimensionless time for Setup 1 and 3 at ports 2 and 5.

Results of Setup 1 and 3 are compared in FIG. 9. The difference in the pressure curves between Setup 1 and 3 is larger than that between Setup 1 and 2 (FIG. 7). These results prove that the test is sensitive enough to show the effect of the nominal gap increase.

The determination of acceptability of the test preform based on the pressure data is of great importance. Whether to accept or reject a particular fiber preform can be decided simply by statistically and/or graphically comparing the transient gas pressure test data for the particular preform with a data base of reference transient gas pressures generated from previous tests of fiber preforms wherein the fiber preforms have been grouped by existence and severity of defect in one of two or more groups that include a standard defect-free group and a defective group, whereby the method determines if the fiber preform or its position in the cavity deviates from the standard defect-free group. The reference data base should be obtained for an identical mold accumulated before the method is practiced to detect a defect in a particular test fiber preform. As long as the data base is generated, there is no need for any priori permeability data. Based on the data base, the reference pressure variation and the allowed deviation from that reference can be determined statistically.

In addition, determination of preform acceptability or not in a high volume production application can be determined by statistical analysis, such as discriminant analysis, which requires that a significant amount of transient gas pressure data sets be available before the analysis [reference 14] in order to group the preform by existence and severity of defect in one of the two or more groups that include a standard defect-free group and a defective group. Discriminant analysis is described in copending application Ser. No. 10/611,318 which is incorporated herein by reference with respect to discriminant analysis techniques.

Moreover, for Setup 2 and 3, the permeabilities of the preform were calculated to be $4.59 \times 10^{-10}$ m$^2$ (a 31% increase in K) and $7.27 \times 10^{-10}$ m$^2$ (a 107% increase in K), respectively. Thus, simple comparison of the permeability values derived from the transient gas pressure data can also be an alternative option when the number of reference data sets is not large enough to conduct the statistical analysis. However, even in such a case, the evalutor needs to examine the pressure curve carefully instead of reducing the entire curve to a single value. The abnormality in permeability of the preform simply implies that there are some unknown anomalies in the flow domain. That is all. Furthermore, the permeability calculation is impractical in multi-dimensional cases with complex geometry since the inverse problem becomes extremely difficult to solve and the cost cannot be justified. In the multi-dimensional case, the evaluator needs to compare the pressure drop at a given time and at a selected port. For example, further results described next below show that the transient pressure curve is very informative.

Figure 10:
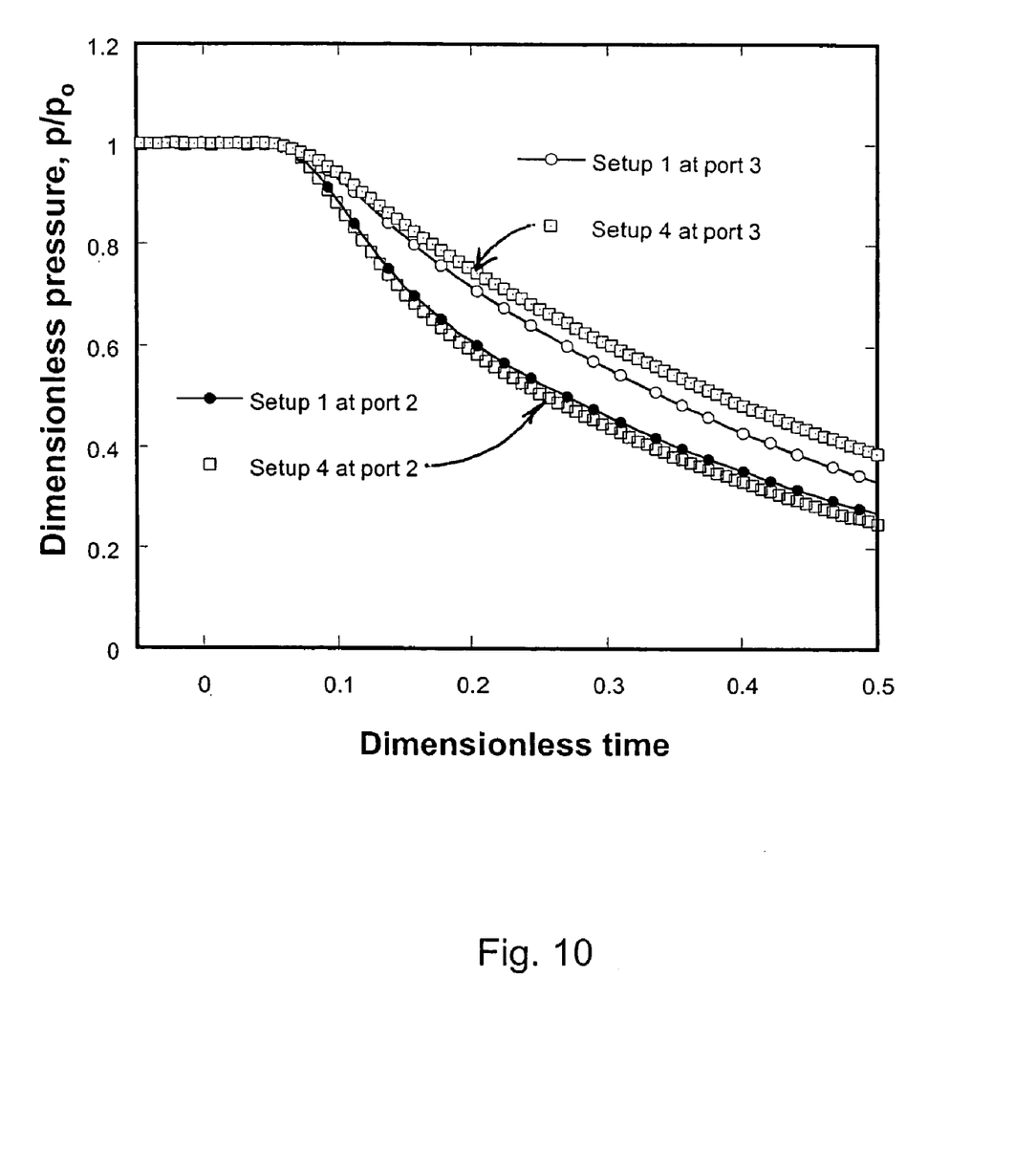
FIG. 10 is a graph of dimensionless gas pressure versus dimensionless time for Setup 1 and 4 at ports 2 and 3.

In particular, results from Setup 1 and 4 at ports 2 and 3 are compared in FIG. 10. The difference is negligible at port 2 but significant at port 3. This leads to the conclusion that an anomaly or obstruction (e.g. the simulated inclusion) is present somewhere between ports 2 and 3. By careful inspection of the pressure curve, the evaluator can locate the place where the anomaly is located.

In the above experimental tests, the preform permeability was determined although it is not necessary in the tests for defect detection. A reference permeability of $K=3.5\times10^{-10}$ $m^2$ was determined without any flow rate measurements by minimizing $S(K)$ in Eq. (8). The transient gas pressure data thus can be used to determine the permeability of the fiber preform without flow rate measurement. This is possible because the gas pressure variation with time has the same characteristics as velocity. The validity of permeability measurement by the gas flow method has been discussed before with regard to the compatibility of Reynolds number and inertial effects in the Darcy region (Re<<1) [see references 7, 9].

As reported in the literature, even in the well-controlled experiments, the permeability can vary by up to 50% for the same kind of preform [references 12, 13]. Thus, a permeability based criterion of preform quality is not always desirable and is sometimes impractical. The method of the invention utilizes the difference of pressure variation during release of pressure at several ports for defect detection and is not based on any permeability comparison. The transient pressure curve pursuant to the invention provides a great deal more information than a single permeability value.

The method of invention is based on transient fluid (e.g. gas) pressure variations for checking the quality of preforms enclosed in an actual or simulated RTM mold prior to resin injection. This method dramatically reduces the uncertainty of the steady state gas flow method by acquiring continuous data over time from multiple ports instead of single data points as in the steady state gas flow method. The method of the invention has general usefulness in detection of anomalies associated with the fiber preform in the preform-receiving cavity, such as racetracking and inclusions in the above examples, prior to resin injection and can be applied to the mass production situation.

Although the invention has been described above in connection with certain embodiments thereof, those skilled in the art will appreciate that various changes, modifications, and the like can be made therein without departing from the spirit and scope of the invention as set forth in the appended claims.

References, which are incorporated herein by reference.

1. Potter, K., *Resin Transfer Molding*, Chapman & Hall, 1997.
2. Kim, S. K., Opperer, J. G. and Daniel, I. M., *Advanced Composite Letters*, 12(3), 109-114, 2003.
3. Opperer, J. G., Kim, S. K. and Daniel, I. M., *Composites Science and Technology* 64 (13-14), 1921-1935, 2004.
4. Liang, Z., Zhang, C., Wang, B. and Shih, C., *45th International SAMPE Symposium*, 2053, 2000.
5. Jaeger, J. C., *Conduction of Heat in Solids* $2^{nd}$ ed., Oxford University Press, 1986.
6. Beck, J. V. and Blackwell, B., *Handbook of Numerical Heat Transfer*, edited by Minkowycz et al., 787, Wiley, 1988
7. Kim, S. K, Opperer, J. G., Kim, D. H and Daniel, I. M., *Polymer Composites*, 24(1): 34-44, 2003.
8. Kim, S. K. and Daniel, I. M., *Composites Part A*, 34, 421-429, 2003.
9. Kim, S. K., Opperer, J. G., and Daniel, I. M., *International Communications in Heat and Mass Transfer*, 29(7), 879-885, 2002.
10. Reklaitis, G. V., Ravindran, A. and Ragsdell, K. M., *Engineering Optimization*, Wiley, New York, 1983.
11. *IMSL Math/Library User's Guide*, Visual Numerics, Houston, 1994.
12. Pamas, R. S., Flynn, K. M., and DalFavero, M. E., *Polymer Composites*, 18(5): 623-633, 1997.
13. Hoes, K., Dinescu, D., Sol, H., Luo, Y., Verpoest, I., and Pamas, R. S., *Proc. Of Third Canadian Conf. on Composites* (CANCOM 2001), Session 2A1, 2001.
14. Klecka, W. R., *Discriminant Analysis*, Sage, Beverly Hills, 1980.

We claim:

1. A method of detecting a defect associated with a fiber preform in a cavity, comprising providing a changing fluid pressure in the cavity containing the fiber preform, measuring time-varying fluid pressures over time at one or more locations of the cavity during changing of the fluid pressure in the cavity, analyzing the measured fluid pressures, or data derived therefrom, to determine membership of the fiber preform in one of two or more groups that include a standard defect-free group and a defective group, determining a defect-free or defective condition of the fiber preform or its position in the cavity using group membership, and conveying the condition to a user for accepting or rejecting the fiber preform or its position in the cavity.

2. The method of claim 1 wherein the changing fluid pressure involves decreasing gas pressure in the cavity over time.

3. The method of claim 2 wherein the gas pressure is decreased in the cavity to ambient pressure after the cavity has been gas pressurized to superambient pressure.

4. The method of claim 1 wherein the changing fluid pressure involves increasing gas pressure in the cavity over time.

5. The method of claim 1 wherein time-varying fluid pressure is measured at one or more ports communicated to the cavity.

6. The method of claim 1 wherein analyzing the fluid pressures, or results derived therefrom, involves statistical analysis to detect an anomaly associated with the fiber preform or its position in the cavity.

7. The method of claim 1 wherein said data derived from the measured time-varying fluid pressures comprises local permeability data of the preform.

8. The method of claim 1 wherein the defective group is associated with a type of defect in the preform or its placement in the cavity.

9. The method of claim 8 wherein the defective group is associated with misplacement of the preform in the cavity.

10. The method of claim 8 wherein the defective group is associated with a race tracking defect associated with a periphery of the preform.

11. The method of claim 8 wherein the defective group is associated with an anomaly in the preform itself.

12. The method of claim 11 wherein the anomaly is associated with an accidental inclusion present in the preform.

13. The method of claim 11 wherein the anomaly is associated with a density variation in the preform.

14. The method of claim 11 wherein the anomaly is associated with a shearing distortion of the preform.

15. The method of claim 1 wherein the analyzing of the measured time-varying fluid pressures, or data derived therefrom, is conducted using a data base generated from previous tests of fiber preforms wherein the fiber preforms have been grouped by existence and severity of defect.

16. The method of claim 1 wherein the preform is evaluated using a one dimensional variation of transient fluid pressures.

17. The method of claim 1 including, after determining the defect-free condition, accepting the preform or its position in the cavity for resin injection.

18. The method of claim 1 including, after determining the defective condition, rejecting the preform or its position in the cavity.

19. A method of detecting a defect associated with a fiber preform in a preform-receiving cavity of a mold or simulated mold, comprising providing a decreasing or increasing gas pressure in the cavity containing the fiber preform, measuring time-varying gas pressures over time at multiple locations of the cavity spaced apart along a dimension of the preform during decreasing or increasing of the gas pressure in the cavity, analyzing the measured time-varying pressures, or data derived therefrom, to determine membership of the fiber preform in one of two or more groups that include a standard defect-free group and a defective group, determining a defect-free or defective condition of the fiber preform or its position in the cavity using group membership, and conveying the condition to a user for accepting or rejecting the preform or its position in the cavity.

20. A method of detecting a defect associated with a fiber preform in a cavity, comprising the steps of changing fluid pressure in the cavity containing the fiber preform, measuring time-varying fluid pressures over time at one or more locations of the cavity during changing of the fluid pressure in the cavity, determining a defect-free or defective condition of the fiber preform or its position in the cavity using the time-varying fluid pressures or data derived therefrom, and conveying the condition to a user for accepting or rejecting the preform or its position in the cavity.

21. Apparatus for detecting a defect associated with a preform in a cavity, comprising a mold or simulated mold having a preform-receiving cavity for receiving a preform, means for changing fluid pressure in the cavity over time, and means for measuring time-varying fluid pressures over time at one or more locations of the cavity to provide time-varying fluid pressures that are analyzable to determine a defect-free or defective condition of the preform or its position in the cavity that is conveyed to a user for accepting or rejecting the preform or its position in the cavity.

22. The apparatus of claim 21 wherein the means for changing fluid pressure comprises a source of pressurized fluid communicated to the cavity via a valve.

23. The apparatus of claim 22 wherein the valve vents the cavity to ambient pressure after the cavity is pressurized to superambient pressure.

24. The apparatus of claim 21 wherein the means for measuring the time-varying pressures comprises one or more ports communicated to the cavity at the one or more locations and a fluid pressure measuring device at the one or more ports.

25. The apparatus of claim 24 wherein the fluid pressure measuring device is a pressure transducer.

* * * * *